(12) United States Patent
Shimabayashi et al.

(10) Patent No.: US 6,274,730 B1
(45) Date of Patent: Aug. 14, 2001

(54) PROCESS FOR PRODUCING HALOGENATED β-LACTAM COMPOUND

(75) Inventors: Akihiro Shimabayashi; Ichirou Kawahara; Shigetoshi Yaguchi; Hiroaki Asai, all of Tokushima (JP)

(73) Assignee: Otsuka Kagaku Kabushiki Kaisha, Osaka (JP)

( * ) Notice: Subject to any disclaimer, the term of this patent is extended or adjusted under 35 U.S.C. 154(b) by 0 days.

(21) Appl. No.: 09/424,259

(22) PCT Filed: Feb. 4, 1999

(86) PCT No.: PCT/JP99/01736

§ 371 Date: Dec. 1, 1999

§ 102(e) Date: Dec. 1, 1999

(87) PCT Pub. No.: WO99/52912

PCT Pub. Date: Oct. 21, 1999

(30) Foreign Application Priority Data

Apr. 9, 1998 (JP) .................................................. 10-116187

(51) Int. Cl.[7] .................... C07D 501/59; C07D 501/16; C07D 501/04; C07D 499/04; C07D 499/865

(52) U.S. Cl. .......................... 540/215; 540/229; 540/230; 540/310

(58) Field of Search ..................................... 540/310, 215, 540/229, 230

(56) References Cited

U.S. PATENT DOCUMENTS 4,276,285    6/1981  Barth .................................... 424/114

OTHER PUBLICATIONS

Ikeda, Chem. Pharm. Bull. 36(1) 218, 1988.*
J. Org. Chem. (1982), 47, pp. 3344–3345, Volkmann et al.
* cited by examiner Primary Examiner—Mark L. Berch
(74) Attorney, Agent, or Firm—Arent Fox Plotkin Kintner Kahn PLLC.

(57) ABSTRACT

A process for preparing halogenated β-lactam compounds, characterized in that a β-lactam amino compound of the formula (1) is reacted with nitrous acid or nitrite in a slurry dispersion state in water, under acid condition in the presence of halogen molecules, thereby obtaining a halogenated β-lactam compound of the formula (4)

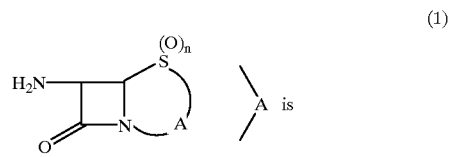

(1)

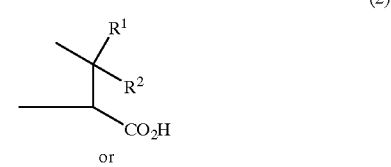

(2)

or

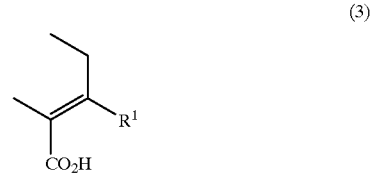

(3)

wherein n is an integer of 0 to 2; A is the formula (2) or (3); $R^1$ and $R^2$ are the same or different and are hydrogen atom, halogen atom, $C_1$~$C_3$ alkyl group, $C_2$~$C_4$ alkenyl group, $C_2$~$C_4$ alkynyl group, nucleophilic group, or $CH_2R^3$; and $R^3$ is halogen atom or nucleophilic group

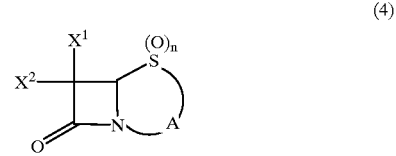

(4)

wherein A is as defined above; $X^1$ is hydrogen atom or halogen atom; and $X^2$ is halogen atom.

5 Claims, No Drawings

PROCESS FOR PRODUCING HALOGENATED β-LACTAM COMPOUND

SPECIFICATION

1. Technical Field

The present invention relates to a process for preparing halogenated β-lactam compounds containing a halogenated penam derivative or halogenated cephem derivative, which are synthetic intermediates for medicine. As an example of halogenated β-lactam compounds obtained by the invention, there is 6,6-dibromopenicillanic acid which is an intermediate for Sulbactam which is a kind of antibacterial agents (JP-A-72115/1980).

2. Background Art

A conventional process for preparing halogenated β-lactam derivatives of the formula (4) by using β-lactam amino compounds of the formula (1), as a starting material, is disclosed in, for example, Volkmann J. Org. Chem. 47, 3344 (1982).

A process for preparing halogenated β-lactam compounds without employing organic solvent is disclosed in Clayton J. Chem. Soc. C 2123 (1969).

In the former process, it is however essential to use a halogenated organic solvent such as methylene chloride or carbon tetrachloride. A large scale use of such a halogenated organic solvent is severely limited in view of safety and environmental pollution problems. The drawbacks of using carbon tetrachloride are its cost and its difficult handling properties. Therefore, a process for preparing halogenated β-lactam compounds in the system using no organic solvent, is highly desired. The latter process employing organic solvent is however impractical because of its remarkably low yield, namely, 34%.

An object of the present invention is to provide a process with which halogenated β-lactam compounds are prepared at high yield and efficiency, in an industrially useful, inexpensive and safe manner, by using water as a reaction solvent, not employing any organic solvent causing many problems in view of safety and environmental pollution.

DISCLOSURE OF THE INVENTION

The present invention provides a process for preparing halogenated β-lactam compounds, characterized in that a lactam amino compound of the formula (1) is reacted with nitrous acid or nitrite in a slurry dispersion state in water, under acid condition in the presence of halogen molecules, thereby obtaining a halogenated β-lactam compound of the formula (4)

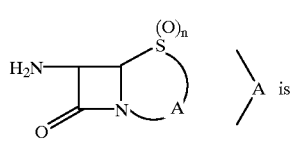

(1)

A is

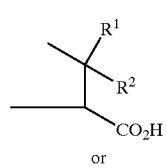

(2)

or

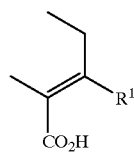

(3)

wherein n is an integer of 0 to 2; A is the formula (2) or (3); $R^1$ and $R^2$ are the same or different and are hydrogen atom, halogen atom, $C_1$–$C_3$ alkyl group, $C_2$–$C_4$ alkenyl group, $C_2$–$C_4$ alkynyl group, nucleophilic group, or $CH_2R^3$; and $R^3$ is halogen atom or nucleophilic group

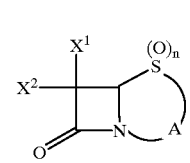

(4)

wherein A is as defined above; $X^1$ is hydrogen atom or halogen atom; and $X^2$ is halogen atom.

The present invention was accomplished when it was discovered that halogenated β-lactam compounds of the formula (4) could be prepared efficiently on a large scale, by reacting β-lactam amino compounds of the formula (1) in a slurry dispersion state in water, after various reaction conditions were considered in order to avoid the use of organic solvents causing many problems in view of safety and environmental pollution, and establish a simple and inexpensive process by using water as a main solvent.

Halogen atoms present in substituent $R^1$, $R^2$ or $R^3$ in the invention are chlorine, bromine and iodine. Examples of $C_1$–$C_3$ alkyl group are methyl, ethyl and propyl. Examples of $C_2$–$C_4$ alkenyl group are vinyl, propenyl, allyl and butenyl. Examples of $C_2$–$C_4$ alkynyl group are ethynyl, propargyl and butynyl.

As nucleophilic groups represented by substituent $R^1$, $R^2$ or $R^3$ in the invention, there are, for example, aliphatic acyloxy groups having 2 to 4 carbon atoms, such as acetyloxy group, propionyloxy group, 3-oxobutyryloxy group, 3-carboxypropionyloxy group and 4-carboxybutyryloxy group; aromatic acyloxy groups such as mandelyloxy group and 2-carboxybenzoyloxy group; carbamoyloxy group; hydroxy group; and mercapto group. Alternatively, these nucleophilic groups may be substituted with an alkyl group having 1 to 3 carbon atoms, or aliphatic acyl group having 1 to 3 carbon atoms. Suitable number of substituents is usually 1 or 2.

Further to the above examples of nucleophilic groups represented by substituent $R^1$, $R^2$ or $R^3$ in the invention, there is a heterocycle bonded through S, that is, heterocyclic thio group. Herein, the heterocycle is a five- or six-member ring containing 1 to 4 heteroatoms selected from O, S or N. Examples of these heterocycles are pyridyl group, pyridazinyl group, pyrazolyl group, thiazolyl group, thiadiazolyl group, triazolyl group and tetrazolyl group. These heterocycles may have a substituent, such as a lower alkyl group having 1 to 3 carbon atoms.

Halogen atoms represented by $X^1$ and $X^2$ of halogenated β-lactam compounds of the formula (4) in the invention are chlorine, bromine and iodine.

In the present invention, acid condition is obtained by adding acid. Examples of acid used are sulfuric acid, hydrohalogenic acid and nitric acid. The amount of acid used to the compounds of the formula (1) is usually 1 to 20 equivalents, preferably 1.5 to 6 equivalents. Examples of halogen molecules used in the invention are bromine, iodine and chlorine. The amount of halogen molecules used to the compounds of the formula (1) is usually 1 to 16 equivalents, preferably 2 to 6 equivalents. Suitable nitrites are sodium nitrite and potassium nitrite. The amount of nitrous acid or nitrite used to the compounds of the formula (1) is usually 1 to 12 equivalents, preferably 2 to 6 equivalents.

The reaction of the invention is usually conducted at atmospheric pressure, but it may be conducted under increased pressure, if required. The reaction temperature is preferably about −10 to 15° C., most preferably −5 to 6° C.

In the present invention, a slurry formed by a compound of the formula (1) and water, or powder of a compound of the formula (1), is preferably added in portions over an adequate time. The reaction time depends on the reaction temperature, substrate concentration and reagent equivalent number, but suitable reaction time is usually about 6 to 36 hours, most desirably 12 to 24 hours.

In the present invention, desired high purity β-lactam compounds can be obtained efficiently by conducting the reaction within a sealed- or unsealed-type container, and filtering a deposited crystal after the reaction is completed. The crystal can also be purified by a usual purification method, such as recrystallization.

BEST MODE OF CARRYING OUT THE INVENTION

The present invention will be described in further detail by giving examples, however, it is to be understood that the invention is not limited to the following examples.

EXAMPLE 1

Preparation of 6,6-dibromopenicillanic acid (4a) [A=(2), $R^1$=$CH_3$, $R^2$=$CH_3$, $X^2$=Br, $X^2$=Br, n=0]

In a 2L four-necked flask, 182 ml of water and 100 g of hydrobromic acid (47% aqueous solution) were mixed and then cooled to below 1° C. To this, 30 ml of bromine and 72 ml of an aqueous solution of sodium nitrite adjusted to be 36%, were added while the temperature at the time of each addition was maintained at below 5° C., thereby obtaining a mixture.

Separately, in another container, 214 ml of water and 40 g of 6-aminopenicillanic acid (1a) [A=(2), $R^1$=$CH_3$, $R^2$=$CH_3$, n=0] were mixed to obtain a 6-aminopenicillanic acid slurry, followed by cooling. This slurry was added in portions, while maintaining its temperature at below 6° C., to the above mixture over 12 hours.

After the above mixed solution was stirred at a temperature below 6° C. for one hour, the gas phase was replaced with air. An aqueous solution of sodium bisulfite was added to a slurry-state reaction solution until it was changed from brown to pale yellow color. The product was filtered and washed with 240 ml of water, to obtain about 61 g of 6,6-dibromopenicillanic acid (4a) (yield: 92%).

NMR, $CDCl_3$(ppm); 1.56(3H, s), 1.65(3H, s), 4.58(1H, s), 5.78(1H, s); IR($cm^{-1}$); 3300(br), 1790, 1763, 1338

EXAMPLE 2

Preparation of 7,7-dibromocephalosporanic acid (4b) [A=(3), $R^1$=$CH_2R^3$, $R^3$=$OCOCH_3$, $X^1$=Br, $X^2$=Br, n=0]

In a 2L four-necked flask, 170 ml of water and 100 g of hydrobromic acid (47% aqueous solution) were mixed and then cooled to below 1° C. To this, 30 ml of bromine and 88 ml of an aqueous solution of potassium nitrite adjusted to be 36%, were added while the temperature at the time of each addition was maintained at below 5° C., thereby obtaining a mixture.

Separately, in another container, 214 ml of water and 50 g of 7-aminocephalosporanic acid (1b) [A=(3), $R^1$=$CH_2R^3$, $R^3$=$OCOCH_3$, n=0] were mixed to obtain a 7-aminocephalosporanic acid slurry, followed by cooling. This slurry was added in portions, while maintaining its temperature at below 6° C., to the above mixture over 14 hours.

After the above mixed solution was stirred at a temperature below 6° C. for one hour, the gas phase was replaced with air. An aqueous solution of sodium bisulfite was added to a slurry-state reaction solution until it was changed from brown to pale yellow color. The product was filtered and washed with 240 ml of water, to obtain about 66 g of 7,7-dibromocephalosporanic acid (yield: 86%)

NMR, $CDCl_3$(ppm); 2.05(3H, s), 3.62(2H, dd), 4.93(2H, dd), 5.04(1H, s); IR($cm^{-1}$); 3350(br), 1795, 1769, 1740.

EXAMPLE 3

Preparation of 7,7-dibromodeacetylcephalosporanic acid (4c) [A=(3), $R^1$=$CH_3$, $X^1$=Br, $X^2$=Br, n=0]

In a 2L four-necked flask, 182 ml of water and 100 g of hydrobromic acid (47% aqueous solution) were mixed and then cooled to below 1° C. To this, 30 ml of bromine and 72 ml of an aqueous solution of sodium nitrite adjusted to be 36%, were added while the temperature at the time of each addition was maintained at below 5° C., thereby obtaining a mixture. Separately, in another container, 214 ml of water and 40 g of 7-aminodeacetylcephalosporanic acid (1c) [A=(3), $R^1$=$CH_3$, n=0] were mixed to obtain a 7-aminodeacetylcephalosporanic acid slurry, followed by cooling. This slurry was added in portions, while maintaining its temperature at below 6° C., to the above mixture over 12 hours.

After the above mixed solution was stirred at a temperature below 6° C. for one hour, the gas phase was replaced with air. An aqueous solution of sodium bisulfite was added to a slurry-state reaction solution until it was changed from brown to pale yellow color. The product was filtered and washed with 240 ml of water, to obtain about 58 g of 7,7-dibromodeacetylcephalosporanic acid (yield: 87%).

NMR, $CDCl_3$(ppm); 2.10(3H, s), 3.75(2H, dd), 5.09(1H, s); IR($cm^{-1}$); 3340(br), 1780, 1762.

EXAMPLE 4

Preparation of 7,7-dibromo-3-(2-methyl-1,3,4-thiadiazole-5-yl)thiomethyl-3-cephem-4-carboxylic acid (4d) [A=(3), $R^1$=$CH_2R^3$, $R^3$=a group of the formula (5), $X^1$=Br, $X^2$=Br, n=0]

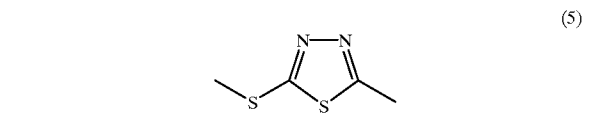

(5)

In a 2L four-necked flask, 182 ml of water and 100 g of hydrobromic acid (47% aqueous solution) were mixed and then cooled to below 1° C. To this, 30 ml of bromine and 72 ml of an aqueous solution of sodium nitrite adjusted to be 36%, were added while the temperature at the time of each addition was maintained at below 5° C., thereby obtaining a mixture.

Separately, in another container, 214 ml of water and 50 g of 7-amino-3-(2-methyl-1,3,4-thiadiazol-5-yl)thiomethyl-3-cephem-4-carboxylic acid (1d) [A=(3), $R^1$=$CH_2R^3$, $R^3$=a group of the formula (5), n=0] were mixed to obtain a 7-amino-3-(2-methyl-1,3,4-thiadiazole-5-yl)thiomethyl-3-cephem-4-carboxylic acid slurry, followed by cooling. This slurry was added in portions, while maintaining its temperature at below 6° C., to the above mixture over 14 hours.

After the above mixed solution was stirred at below 6° C. for one hour, the gas phase was replaced with air. An aqueous solution of sodium bisulfite was added to a slurry-state reaction solution until it was changed from brown to pale yellow color. The product was filtered and washed with 240 ml of water, to obtain about 60 g of 7,7-dibromo-3-(2-methyl-1,3,4-thiadiazole-5-yl)thiomethyl-3-cephem-4-carboxylic acid (yield: 85%).

NMR, $CDCl_3$(ppm); 2.60(3H, s), 3.98(2H, dd), 4.58(2H, dd), 5.29(1H, s); IR($cm^{-1}$); 3300(br), 1780, 1766.

EXAMPLE 5

Preparation of 6,6-diiodopenicillanic acid (4e) [A=(2), $R^1$=$CH_3$, $R^2$=$CH_3$, $X^1$=I, $X^2$=I, n=0]

In a 2L four-necked flask, 150 g of water and 160 g of hydriodic acid (47% aqueous solution) were mixed and then cooled to below 1° C. To this, 150 g of iodine and 72 ml of an aqueous solution of sodium nitrite adjusted to be 36%, were added while the temperature at the time of each addition was maintained at below 5° C., thereby obtaining a mixture. Separately, in another container, 214 ml of water and 40 g of 6-aminopenicillanic acid (1e) [A=(2), $R^1$=$CH_3$, $R^2$=$CH_3$, n=0] were mixed to obtain a 6-aminopenicillanic acid slurry, followed by cooling. This slurry was added in portions, while maintaining its temperature at below 6° C., to the above mixture over 12 hours.

After the above mixed solution was stirred at a temperature below 6° C. for one hour, the gas phase was replaced with air. An aqueous solution of sodium bisulfite was added to a slurry-state reaction solution until it was changed from brown to pale yellow color. The product was filtered and washed with 240 ml of water, to obtain about 74 g of 6,6-diiodopenicillanic acid (yield: 88%).

NMR, $CDCl_3$(ppm); 1.50(3H, s), 1.61(3H, s), 4.25(1H, s), 5.48(1H, s); IR($cm^{-1}$); 3320(br), 1785, 1760, 1320.

REFERENCE EXAMPLE 1

Preparation of 6,6-dibromopenicillanic acid-1,1-dioxide [A=(2), $R^1$=$CH_3$, $R^2$=$CH_3$, $X^1$=Br, $X^2$=Br, n=2]

In a 2L four-necked flask, 70 g of 6,6-dibromopenicillanic acid (4a) [A=(2), $R^1$=$CH_3$, $R^2$=$CH_3$, $X^1$=Br, $X^2$=Br, n=0] and 500 ml of water were added, to which 105 ml of 3N sodium hydroxide was then added over 30 minutes. The 6,6-dibromopenicillanic acid was dissolved, and pH was stabilized at 7.0. This solution was cooled to −5° C., and a premix solution of potassium permanganate (prepared using 59.3 g of potassium permanganate, 18 ml of a concentrated phosphoric acid and 600 ml of water) was added thereto until pink color remained. Upon completion of addition, 500 ml of ethyl acetate was added thereto, and 105 ml of 6N hydrochloric acid was added so that pH was lowered to 1.23. Thereafter, 250 ml of 1M sodium bisulfate was added thereto at about 10° C. over 10 to 15 minutes, while maintaining pH of 1.25 to 1.35 with 6N hydrochloric acid. The aqueous phase was saturated with sodium chloride. The organic phase was separated, and the aqueous phase was extracted twice with each of 150-ml ethyl acetate. These ethyl acetate solutions were united and dried with magnesium sulfate. In this solution, 70 g of 6,6-dibromopenicillanic acid-1,1-dioxide was contained (yield: 92%).

NMR, DMSO-$d_6$(ppm); 1.38(3H, s), 1.48(3H, s), 4.69 (1H, s), 6.01(1H, s); IR($cm^{-1}$); 3400(br), 1818, 1754.

REFERENCE EXAMPLE 2

Preparation of penicillanic acid-1,1-dioxide (Sulbactam)

To an ethyl acetate solution of 70 g of 6,6-dibromopenicillanic acid-1,1-dioxide [A=(2), $R^1$=$CH_3$, $R^2$=$CH_3$, $X^1$=Br, $X^2$=Br, n=2] obtained in Reference Example 1, 705 ml of saturated sodium hydrogencarbonate was added and further 8.9 g of 5% palladium/activated carbon catalyst was added. This mixture was stirred at pressure of about 5 kg/$cm^2$ in an atmosphere of hydrogen, for one hour. This catalyst was filtered off, and the aqueous phase of the filtrate was adjusted to pH 1.2 with 6N hydrochloric acid. This aqueous phase was saturated with sodium chloride. The organic phase was separated, and the aqueous phase was extracted three times with each of 200-ml ethyl acetate. These ethyl acetate solutions were united and dried with magnesium sulfate, followed by vacuum evaporation, resulting in 33.5 g of a crystal of penicillanic acid-1,1-dioxide (yield: 80%).

NMR, DMSO-$d_6$(ppm); 1.36(3H, s), 1.46(3H, s), 4.41 (2H, dd), 4.24(1H, s), 5.17(1H, dd); IR($cm^{-1}$); 3380(br), 1780, 1600.

COMPARATIVE EXAMPLE 1 (ORGANIC SOLVENT METHOD)

Preparation of 6,6-dibromopenicillanic acid

In a 2L four-necked flask, 67 ml of carbon tetrachloride, 107 ml of water and 44 ml of diluted sulfuric acid (70% aqueous solution) were mixed and then cooled to below 1° C. To this, 20 ml of bromine and 44 ml of an aqueous solution of sodium nitrite adjusted to be 36%, were added while the temperature at the time of each addition was maintained at below 5° C., thereby obtaining a mixture.

Separately, in another container, 170 ml of carbon tetrachloride and 40 g of 6-aminopenicillanic acid (1a) [A=(2), $R^1$=$CH_3$, $R^2$=$CH_3$, n=0] were mixed to obtain a 6-aminopenicillanic acid slurry, followed by cooling. This slurry was added in portions, while maintaining its temperature at below 6° C., to the above mixture over 12 hours.

After the above mixed solution was stirred at below 6° C. for one hour, the gas phase was replaced with air. An aqueous solution of sodium bisulfite was added to a slurry-state reaction solution until it was changed from brown to pale yellow color. The product was filtered, washed with 40 ml of carbon tetrachloride, and with 240 ml of water, to obtain about 47 g of 6,6-dibromopenicillanic acid (yield: 71%).

NMR and IR data of 6,6-dibromopenicillanic acid were the same as in Example 1.

COMPARATIVE EXAMPLE 2 (ORGANIC SOLVENT METHOD)

Preparation of 6,6-dibromopenicillanic acid

In a 2L four-necked flask, 67 ml of methylene chloride, 107 ml of water and 44 ml of diluted sulfuric acid (70% aqueous solution) were mixed and then cooled to below 10° C. To this, 20 ml of bromine and 44 ml of an aqueous solution of sodium nitrite adjusted to be 36%, were added while the temperature at the time of each addition was maintained at below 5° C., thereby obtaining a mixture.

Separately, in another container, 170 ml of methylene chloride and 40 g of 6-aminopenicillanic acid (1a) [A=(2), $R^1$=$CH_3$, $R^2$=$CH_3$, n=0] were mixed to obtain a 6-aminopenicillanic acid slurry, followed by cooling. This slurry was added in portions, while maintaining its temperature at below 6° C., to the above mixture over 12 hours.

After the above mixed solution was stirred at a temperature below 6° C. for one hour, the gas phase was replaced with air. An aqueous solution of sodium bisulfite was added to a slurry-state reaction solution until it was changed from brown to pale yellow color. The product was filtered, washed with 40 ml of methylene chloride, and with 240 ml of water, to obtain about 40 g of 6,6-dibromopenicillanic acid (yield: 60%).

NMR and IR data of 6,6-dibromopenicillanic acid were the same as in Example 1.

INDUSTRIAL APPLICABILITY

According to the present invention, it is possible to provide a process with which halogenated β-lactam compounds are prepared at high yield and efficiency, in an industrially useful, inexpensive and safe manner, by using water as a reaction solvent, not employing any organic solvent causing many problems in view of safety and environmental pollution.

What is claimed is:
1. A process for preparing halogenated β-lactam compounds, wherein a β-lactam amino compound of the formula (1)

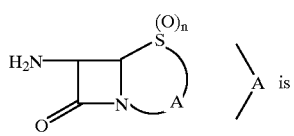

(1)

A is

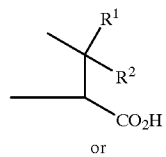

(2)

or

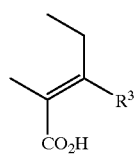

(3)

wherein
n is an integer of 0 to 2;
A is the formula (2) or (3);
$R^1$ and $R^2$ are the same or different, and are a hydrogen atom, a halogen atom, a $C_1$–$C_3$ alkyl group, a $C_2$–$C_4$ alkenyl group, a $C_2$–$C_4$ alkynyl group, an aliphatic carboxylic acyloxy group having 2 to 4 carbon atoms, an aromatic acyloxy group, a carbamoyloxy group, a hydroxy group, or a mercapto group, or an above group substituted with an alkyl group having 1 to 3 carbon atoms or aliphatic carboxylic acyl group having 1 to 3 carbon atoms, a heterocyclic thio group substituted with an alkyl group having 1 to 3 carbon atoms, or $CH_2R^3$; and $R^3$ is a halogen atom, an aliphatic carboxylic acyloxy group having 2 to 4 carbon atoms, an aromatic acyl group, a carbamoyloxy group, a hydroxy group, a mercapto group, or an above group substituted with an alkyl group having 1 to 3 carbon atoms or an aliphatic carboxylic acyl group having 1 to 3 carbon atoms, or a heterocyclic thio group substituted with an alkyl group having 1 to 3 carbon atoms, further wherein the heterocycle of the heterocyclic thio group of $R^1$, $R^2$ and $R^3$ is a five- or six-member ring containing 1 to 4 heteroatoms selected from O, S, or N;

is reacted with nitrous acid or a salt of a nitrous acid in a slurry dispersion state in water, under acid condition in the presence of halogen molecules, thereby obtaining a halogenated β-lactam compound of the formula (4)

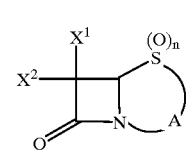

(4)

wherein A is as defined above;
$X^1$ is a hydrogen atom or a halogen atom; and
$X^2$ is a halogen atom.

2. A process as defined in claim 1 wherein the halogen molecule is bromine, iodine or chlorine.

3. The process as defined in claim 1 wherein the group represented by $R^1$, $R^2$ or $R^3$ is an aliphatic carboxylic acyloxy group having 2 to 4 carbon atoms, an aromatic acyloxy group, a carbamoyloxy group, a hydroxy group, a mercapto group, or an above group substituted with an alkyl group having 1 to 3 carbon atoms or an aliphatic carboxylic acyl group having 1 to 3 carbon atoms.

4. The process as defined in claim 1 wherein the group represented by $R^1$, $R^2$ or $R^3$ is a heterocyclic thio group, or heterocyclic thio group substituted by an alkyl group having 1 to 3 carbon atoms, further wherein the heterocycle of the heterocyclic thio group is a five- or six-member ring containing 1 to 4 heteroatoms selected from O, S or N.

5. The process as defined in claim 4 wherein the heterocycle is a pyridyl group, a pyridazinyl group, a pyrazolyl group, a thiazolyl group, a thiadiazolyl group, a triazolyl group or tetrazolyl group.

* * * * *